US006989276B2

(12) United States Patent
Thompson et al.

(10) Patent No.: US 6,989,276 B2
(45) Date of Patent: Jan. 24, 2006

(54) RAPID CLASSIFICATION OF BIOLOGICAL COMPONENTS

(75) Inventors: Vicki S. Thompson, Idaho Falls, ID (US); Karen B. Barrett, Meridian, ID (US); Diane E. Key, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 551 days.

(21) Appl. No.: 10/017,577

(22) Filed: Dec. 14, 2001

(65) Prior Publication Data

US 2002/0168699 A1 Nov. 14, 2002

Related U.S. Application Data

(60) Provisional application No. 60/290,256, filed on May 10, 2001.

(51) Int. Cl.
  *G01N 33/543* (2006.01)

(52) U.S. Cl. .................. 436/518; 436/538; 436/540; 435/7.1; 435/7.92; 435/7.93; 435/971; 435/973; 435/975; 422/50; 422/56; 422/57; 422/60; 424/130.1

(58) Field of Classification Search ............... 436/518, 436/538, 540; 435/7.1, 7.92, 7.93, 971, 973, 435/975; 422/50, 56, 57, 60; 424/130.1
See application file for complete search history.

(56) References Cited

U.S. PATENT DOCUMENTS

| 566,558 A | 8/1896 | Bell ................... 435/287.2 |
| 4,542,104 A | 9/1985 | Stryer et al. |
| 4,880,750 A | 11/1989 | Francoeur ............... 436/501 |
| 5,270,167 A | 12/1993 | Francoeur .............. 435/7.21 |

(Continued)

FOREIGN PATENT DOCUMENTS

| WO | WO 86/02734 | 10/1985 | ............... 33/53 |
| WO | WO 90/05296 | 10/1989 | ............... 21/66 |
| WO | WO 97/29206 | 2/1997 | ............... 19/30 |
| WO | WO 99/38985 | 1/1999 | |

OTHER PUBLICATIONS

A. M. Francoeur et al., 136 J. Immunol 1648 (1986).
S. Cabilly, Combinatorial Peptide Library Protocols (Humana Press, pp. 129–154, 1997.
G. M. Santangelo et al., Cloning of Open Reading Frames and Promoters from the *Saccharomyces cerevisiae* Genome: Construction of Genomic Libraries of Random Small Fragments, 46 Gene 181–186 (1986).
S.S. Wong, Chemistry of Protein Conjugation and Cross–Linking (CRC Press, entire book, 1991).
N. E. Good & S. Izawa, Hydrogen Ion Buffers, 24 Methods Enzymology 53–68 (1972).
D. M. Kemeny & S. J. Challacombe, ELISA and Other Solid Phase Immunoassays (1988).
R. C. Boguslaski et al., Clinical Immunochemistry: Principles of Methods and Applications (1984).
D. P. Stites et al, Basic and Clinical Immunology (1994).
I. Hemmila, Fluoroimmunoassays and Immunofluorometric Assays, 31 Clin. Chem. 359 (1985).
W. Schramm, et al., Drugs of Abuse in Saliva: A Review, 16 J. Anal. Toxicology 1–9 (1992).
E. J. Cone, Saliva Testing for Drugs of Abuse, 694 Ann. N. Y. Acad. Sci. 91–127 (1995).
D. A. Kidwell et al, Testing for drugs of abuse in saliva and sweat, 713 J. Chrom. B 111–135 (1998).
V. S. Thompson et al., Antibody profiling as an identification tool for forensic samples, 3576 Investigation and Forensic Science Technologies 52–59 (1999).
S. B Karch, Drug Abuse Handbook (CRC Press, 1998).
L. D. Bowers, Athletic Drug Testing, 17 Sports Pharmacology 299–318 (1998).
Parry, Tests for HIV and hepatitis viruses, 694 Annals N. Y Acad. Sci. 221 (1993).
M. Peat & A.E. Davis, Drug Abuse Handbook (CRC Press, Boca Raton, Fla. 1998).
Larry D. Bowers, Ph.D. Athletic Drug Testing, Sport Pharmacology, pp. 299–319.
Cambridge Healthtech Institute's Fourth Annual, DNA Forensics (Brochure).
Jeffrey Baird, Forensic DNA in the Trial Court 19909–1992: A Brief History, pp. 61–75.
Controversy Over Forensic DNA Analysis, Science in the Courtroom, QC Researcher, pp. 924–925.
John McCabe, DNA Fingerprinting: The Failings of Frye, pp. 455–481.
International Search Report, dated Feb. 21, 2003.

(Continued)

*Primary Examiner*—Long V. Le
*Assistant Examiner*—Lisa V. Cook
(74) *Attorney, Agent, or Firm*—Trask Britt PC

(57) ABSTRACT

A method is disclosed for analyzing a biological sample by antibody profiling for identifying forensic samples or for detecting the presence of an analyte. In an illustrative embodiment of the invention, the analyte is a drug, such as marijuana, cocaine, methamphetamine, methyltestosterone, or mesterolone. The method involves attaching antigens to the surface of a solid support in a preselected pattern to form an array wherein the locations of the antigens are known; contacting the array with the biological sample such that a portion of antibodies in the sample reacts with and binds to antigens in the array, thereby forming immune complexes; washing away antibodies that do form immune complexes; and detecting the immune complexes, thereby forming an antibody profile. Forensic samples are identified by comparing a sample from an unknown source with a sample from a known source. Further, an assay, such as a test for illegal drug use, can be coupled to a test for identity such that the results of the assay can be positively correlated to the subject's identity.

14 Claims, 4 Drawing Sheets

U.S. PATENT DOCUMENTS

| | | |
|---|---|---|
| 5,445,934 A | 8/1995 | Fodor et al. .................... 435/6 |
| 5,541,113 A | 7/1996 | Siddigi et al. ................ 436/56 |
| 5,605,662 A | 2/1997 | Heller et al. ............... 422/68.1 |
| 5,744,305 A | 4/1998 | Fodor et al. |
| 5,858,801 A | 1/1999 | Brizzolara |
| 5,885,780 A | 3/1999 | Olivera et al. ............... 435/7.1 |
| 6,103,479 A | 8/2000 | Taylor |

OTHER PUBLICATIONS

Thompson et al., "A Novel Test for Detection of Drugs in the Body That Also Provides the Identity of the Person Being Examined," *ONDCP International Technology Symposium, Counterdrug Research and Development: Technologies for the Next Decade, San Diego, Jun. 25–28, 2001.*

Thompson et al., "Forensic Validation Study of Antibody Profiling Identification," *FRENZY—Forensic Science and Crime Scene Technology, Conference and Expo, Washington, D.C., May 14–17, 2001.*

Thompson et al., "Novel Assay for Drug and Identity Determination in Body Fluids," *American Academy of Forensic Sciences Annual Meeting, Reno, Feb. 22–26, 2000.*

Thompson et al., "Antibody Profiling Technique for Rapid Identification of Forensic Samples," *CAT/NWAFS/SWAFS/SAT Combined Professional Training Seminar, Las Vegas, Nov. 3–7, 1997.*

Thompson et al., "Antibody Profiling Technique for Rapid Identification of Forensic Samples," *California Association of Criminalists Fall Seminar, Irvine, California, Oct. 8–11, 1997.*

R. M. Bernstein, Cellular Protein & RNA Antigens in Autoimmune Disease, 2 Mol. Biol. Med., 105–120, 1984.

P. S. Fodor, 277 Science 393–395 (1997).

S. E. Cwirla et al, Peptides on Phage: A Vast Library of Peptides for Identifying Ligands, 87 Proc. Nat'l Acad. Sci. USA 6378–6382 (1990).

K. S. Lam et al., A New Type of Synthetic Peptide Library for Identifying Ligand–binding Activity, 354 Nature 82–84 (1991).

R. A. Young & R. W. Davis, Yeast RNA Polymerase II Genes: Isolation with Antibody Probes, 222 Science 778–782 (1983).

Thompson and Maragos, 44 J. Agric, Food Chem., 1041–1046 (1996).

T. Persoon, Immunochemical Assays in the Clinical Laboratory, 5 Clinical Laboratory Science 31 (1992).

J.K. Leland et al., Electrogenerated Chemiluminescense: An Oxidative–Reduction Type ECL Reactions Sequence Using Triprophyl Amine, 137 J. Electrochemical Soc. 3127–3131 (1990).

Miragen Antibody Profile Assay Advertisement.

David P. Ascher and Chester Roberts, Determination of the Etiology of Seroreversals in HIV Testing by Antibody Fingerprinting, Journal of Acquired Immune Deficiency Syndromes, 6:241–244 1993 Raven Press, Ltd, NY.

Ann–Michele Francoeur, Antibody Fingerprinting: A Novel Method For Identifying Individual People and Animals, Miragen, Inc., 822–825.

Thomas F. Unger, PhD and Arthur Strauss, MD FAAP, Individual–Specific Antibody Profiles as a Means of Newborn Infant Identification, Journal of Perinatology vol. 15, No. 2, 1995.

James K. Scott and George P. Smith, Searching for Peptide Ligands with an Epitope Library, Science, vol. 249, 386–390.

James J. Devlin, Lucy C. Panganiban, Patricia E. Devlin, Random Peptide Libraries: A Source of Specific Protein Binding Molecules, Science, vol. 249, 404–406 & 336–337.

RAPID CLASSIFICATION OF BIOLOGICAL COMPONENTS

RELATED APPLICATION

This application claims priority to U.S. Patent Application Ser. No. 60/290,256, filed May 10, 2001, and is incorporated herein.

CONTRACTUAL ORIGIN OF THE INVENTION

The United States Government has certain rights in this invention pursuant to Contract No. DE-AC07-99ID13727, and Contract No. DE-AC07-05ID14517 between the United States Department of Energy and Battelle Energy Alliance, LLC.

BACKGROUND OF THE INVENTION

This invention relates to assaying biological samples. More particularly, the invention relates to methods for analyzing biological samples comprising antibody profiling. In an illustrative embodiment of the invention, the analyzing of biological samples comprises a combination of antibody profiling for characterizing individual specific antibodies in the biological samples and simultaneous assay of an analyte in the biological samples.

Many methods are known for identifying individuals or biological samples obtained from such individuals. For example, blood typing is based on the existence of antigens on the surface of red blood cells. The ABO system relates to four different conditions with respect to two antigens, A and B. Type A individuals exhibit the A antigen; Type B individuals exhibit the B antigen; Type AB individuals exhibit both the A and B antigens; and Type O individuals exhibit neither the A nor the B antigen. By analyzing a sample of a person's blood, it is possible to classify the blood as belonging to one of these blood groups. While this method may be used to identify one individual out of a small group of individuals, the method is limited when the group of individuals is larger because no distinction is made between persons of the same blood group. For example, the distribution of the ABO blood groups in the U.S. is approximately 45% O, 42% A, 10% B, and 3% AB. Tests based on other blood group antigens or isozymes present in body fluids suffer from the same disadvantages as the ABO blood typing tests. These methods can exclude certain individuals, but cannot differentiate between members of the same blood group.

A variety of immunological and biochemical tests based on genetics are routinely used in paternity testing, as well as for determining the compatibility of donors and recipients involved in transplant or transfusion procedures, and also sometimes as an aid in the identification of humans and animals. For example, serological testing of proteins encoded by the human leukocyte antigen (HLA) gene locus is well known. Although a good deal of information is known concerning the genetic makeup of the HLA locus, there are many drawbacks to using HLA serological typing for identifying individuals in a large group. Each of the HLA antigens must be tested for in a separate assay, and many such antigens must be assayed to identify an individual, an arduous process when identifying one individual in a large group.

In the past decade, DNA-based analysis techniques, such as restriction fragment length polymorphisms (RFLPs) and polymerase chain reaction (PCR) have rapidly gained acceptance in forensic and paternity analyses for matching biological samples to an individual. RFLP techniques are problematic, however, due to the need for relatively large sample sizes, specialized equipment, highly skilled technicians, and lengthy analysis times. For forensic applications there is often not enough sample available for this type of assay, and in remote areas the necessary equipment is often not available. In addition, this technique can take from two to six weeks for completion and can result in costly delays in a criminal investigation. Moreover, the cost of RFLP analysis can be prohibitory if screening of many samples is necessary. PCR techniques have the advantages over RFLP analysis of requiring much smaller sample sizes and permitting more rapid analysis, but they still require specialized equipment and skilled technicians, and they are also expensive.

U.S. Pat. No. 4,880,750 and U.S. Pat. No. 5,270,167 disclose "antibody profiling" or "AbP" as a method that overcomes many of the disadvantages associated with DNA analysis. Antibody profiling is based on the discovery that every individual has a unique set of antibodies present in his or her bodily fluids. R. M. Bernstein et al., Cellular Protein and RNA Antigens in Autoimmune Disease, 2 Mol. Biol. Med. 105–120 (1984). These antibodies, termed "individual-specific antibodies" or "ISAs," have been found in blood, serum, saliva, urine, semen, perspiration, tears, and body tissues. A. M. Francoeur, Antibody Fingerprinting: A Novel Method for Identifying Individual People and Animals, 6 Bio/technology 821–825 (1988). ISAs are not associated with disease and are thought to be directed against cellular components of the body. Every person is born with an antibody profile that matches the mother's antibody profile. T. F. Unger & A. Strauss, Individual-specific Antibody Profiles as a Means of Newborn Infant Identification, 15 J. Perinatology 152–155 (1995). The child's antibody profile gradually changes, however, until a stable unique pattern is obtained by about two years of age. It has been shown that even genetically identical individuals have different antibody profiles. An individual's profile is apparently stable for life and is not affected by short-term illnesses. A. M. Francoeur, supra. Few studies have been conducted on individuals with long-term diseases. Preliminary results, however, indicate that, although a few extra bands may appear, the overall pattern remains intact. This technique has been used in the medical field to track patient samples and avoid sample mix-ups. In addition, the technique has been used in hospitals in cases where switching of infants or abduction has been alleged. The method has a number of advantages over DNA techniques, including low cost, rapid analysis (2 hours from the time the sample is obtained), and simplicity (no special equipment or training is necessary). In addition, this method will potentially work on samples that contain no DNA.

WO 97/29206 discloses a method for identifying the source of a biological sample used for diagnostic testing by linking diagnostic test results to an antibody profile of the biological sample. By generating an antibody profile of each biological sample, the origin of the biological sample is identified.

Many assays are now available that use the attachment of specific nucleic acid probes or other biological molecules to surfaces such as glass, silicon, polymethacrylate, polymeric filters, microspheres, resins, and the like. In a configuration where the surface is planar, these assays are sometimes referred to as "biochips." Initially, biochips contained nucleic acid probes attached to glass or silicon substrates in microarrays. These DNA chips are made by microfabrication technologies initially developed for use in computer chip manufacturing. Leading DNA chip technologies include an in situ photochemical synthesis approach, P. S. Fodor, 277 Science 393–395 (1997); U.S. Pat. No. 5,445,934; an electrochemical positioning approach, U.S. Pat. No. 5,605,662; depositing gene probes on the chip using a sprayer that resembles an ink-jet printer; and the use of gels in a solution-based process. Arrays of other types of molecules, such as peptides, have been fabricated on biochips, e.g., U.S. Pat. No. 5,445,934.

While the known methods for using antibody profiling are generally suitable for their limited purposes, they possess certain inherent deficiencies that detract from their overall utility in analyzing, characterizing, and identifying biological samples. For example, the known methods rely on fractionation of antigens by electrophoresis and then transfer of the fractionated antigens to a membrane. Due to differences in conditions from one fractionation procedure to another, there are lot-to-lot differences in the positions of the antigens on the membrane such that results obtained using membranes from one lot cannot be compared with results obtained using membranes from another lot. Further, when colorimetric procedures are used for detecting immune complexes on the membrane, color determination can be subjective such that results may be interpreted differently by different observers.

In view of the foregoing, it will be appreciated that providing a method for analyzing biological samples, wherein lot-to-lot differences in reagents and subjectivity do not affect interpretation of results, would be a significant advancement in the art. More particularly, it would be advantageous to provide a method for analyzing biological samples by antibody profiling in a biochip format such that analysis would be amenable to automation.

BRIEF SUMMARY OF THE INVENTION

An illustrative embodiment of the invention comprises a method for analyzing biological material including individual-specific antibodies, comprising: forming an array of multiple antigens by attaching the multiple antigens to the surface of a solid support in a preselected pattern such that the locations of the multiple antigens are known; obtaining a sample of the biological material and contacting the array with the sample such that a portion of the individual-specific antibodies contained in the sample reacts with and binds to antigens in the array, thereby forming immune complexes; washing the solid support containing the immune complexes such that antibodies in the sample that do not react with and bind to the antigens in the array are removed; and detecting the immune complexes and determining the locations thereof such that an antibody profile is obtained.

Illustratively, the detecting of the immune complexes comprises treating the solid support having immune complexes attached thereto such that the presence of immune complexes at a location is characterized by a color change as compared to the absence of immune complexes at the location. In one illustrative embodiment, the process of detecting the immune complexes further comprises monitoring the solid support with solid state color detection circuitry for comparing the color patterns before and after contacting the array with the sample. In another illustrative embodiment, the process of detecting the immune complexes further comprises obtaining a color camera image before and after contacting the array with the sample and analyzing pixel information obtained therefrom. In still another illustrative embodiment of the invention, the solid support is a surface plasmon resonance chip and the detecting of the immune complexes further comprises scanning the surface plasmon resonance chip before and after contacting the array with the sample and comparing data obtained therefrom. In yet another illustrative embodiment of the invention, the detecting of immune complexes comprises obtaining an image using a charge-coupled device to detect the color change comprising fluorescence emission.

In yet another illustrative embodiment of the invention, the method is used as a test for use of drugs. Still another illustrative embodiment of the invention involves analysis of an antibody profile obtained from a forensic sample and comparison with an antibody profile obtained from a sample from a criminal suspect or victim of crime.

DETAILED DESCRIPTION

Figure 1:
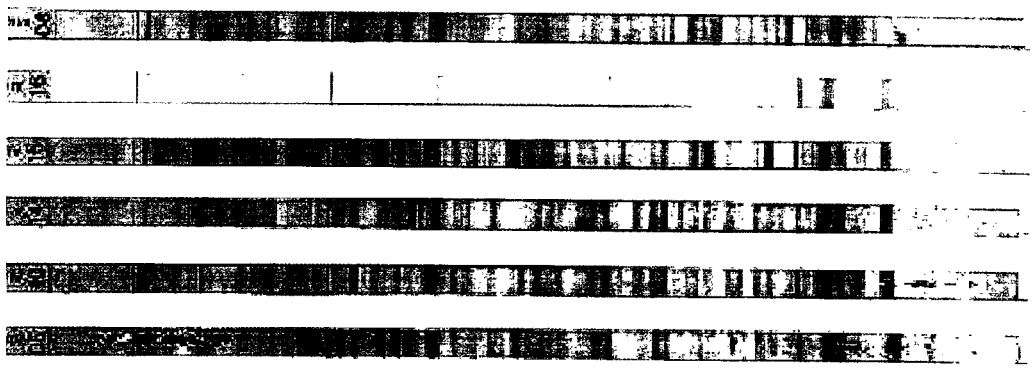
FIG. 1 shows illustrative antibody profiles obtained from saliva samples according to the procedure of Example 1.

Before the present methods for analyzing biological samples are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the"

include plural referents unless the context clearly dictates otherwise. Thus, for example, reference to a method for analyzing a biological sample from "an animal" includes reference to two or more of such animals, reference to "a solid support" includes reference to one or more of such solid supports, and reference to "an array" includes reference to two or more of such arrays.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

As used herein, "solid support" means a generally or substantially planar substrate onto which an array of antigens is disposed. A solid support can be composed of any material suitable for carrying the array. Materials used to construct these solid supports need to meet several requirements, such as (1) the presence of surface groups that can be easily derivatized, (2) inertness to reagents used in the assay, (3) stability over time, and (4) compatibility with biological samples. For example, suitable materials include glass, silicon, silicon dioxide (i.e., silica), plastics, polymers, hydrophilic inorganic supports, and ceramic materials. Illustrative plastics and polymers include poly (tetrafluoroethylene), poly(vinylidenedifluoride), polystyrene, polycarbonate, polymethacrylate, and combinations thereof. Illustrative hydrophilic inorganic supports include alumina, zirconia, titania, and nickel oxide. An example of a glass substrate would be a microscope slide. Silicon wafers used to make computer chips have also been used to make biochips. E.g., U.S. Pat. No. 5,605,662.

As used herein, "array" means an arrangement of locations on the solid support. The locations will generally be arranged in two-dimensional arrays, but other formats are possible. The number of locations can range from several to at least hundreds of thousands. The array pattern and spot density can vary. For example, using a commercially available GMS 417 Arrayer from Genetic Microsystems (Woburn, Mass.) the spot size and density can be selected by the user. With spots of 150 $\mu$m diameter and 300 $\mu$m center-to-center spacing, more than 1000 spots can be placed in a square centimeter and more than 10,000 spots can be placed on a standard microscope slide. With 200 $\mu$m center-to-center spacing, these numbers increase to 2500 per square centimeter and more than 25,000 per slide.

As used herein, "colorigenic" refers to a substrate that produces a colored product upon digestion with an appropriate enzyme. Such colored products include fluorescent and luminescent products.

A first step in the present method is to prepare an array of antigens by attaching the antigens to the surface of the solid support in a preselected pattern such that the locations of antigens in the array are known. As used herein, an antigen is a substance that is bound by an antibody. Antigens can include proteins, carbohydrates, nucleic acids, hormones, drugs, receptors, tumor markers, and the like, and mixtures thereof. An antigen can also be a group of antigens, such as a particular fraction of proteins eluted from a size exclusion chromatography column. Still further, an antigen can also be identified as a designated clone from an expression library or a random epitope library.

In one illustrative embodiment of the invention, antigens are isolated from HeLa cells as generally described in A. -M. Francoeur et al., 136 J. Immunol. 1648 (1986). Briefly, HeLa cells are grown in standard medium under standard tissue culture conditions. Confluent HeLa cell cultures are then rinsed, preferably with phosphate-buffered saline (PBS), lysed with detergent, and centrifuged to remove insoluble cellular debris. The supernate contains approximately 10,000 immunologically distinct antigens suitable for generating an array.

There is no requirement that the antigens used to generate the array be known. All that is required is that the source of the antigens be consistent such that a reproducible array can be generated. For example, the HeLa cell supernate containing the antigens can be fractionated on a size exclusion column, electrophoretic gel, density gradient, or the like, as is well known in the art. Fractions are collected, and each fraction collected could represent a unique set of antigens for the purpose of generating the array. Thus, even though the antigens are unknown, a reproducible array can be generated if the HeLa cell antigens are isolated and fractionated using the same method and conditions.

Other methods, such as preparation of random peptide libraries or epitope libraries are well known in the art and may be used to reproducibly produce antigens. E.g., J. K. Scott & G. P. Smith, Searching for Peptide Ligands with an Epitope Library, 249 Science 386 (1990); J. J. Devlin et al., Random Peptide Libraries: A Source of Specific Protein Binding Molecules, 249 Science 404–406 (1990); S. E. Cwirla et al., Peptides on Phage: A Vast Library of Peptides for Identifying Ligands, 87 Proc. Nat'l Acad. Sci. USA 6378–6382 (1990); K. S. Lam et al., A New Type of Synthetic Peptide Library for Identifying Ligand-binding Activity, 354 Nature 82–84 (1991); S. Cabilly, Combinatorial Peptide Library Protocols (Humana Press, 304 pp, 1997); U.S. Pat. No. 5,885,780. Such libraries can be constructed by ligating synthetic oligonucleotides into an appropriate fusion phage. Fusion phages are filamentous bacteriophage vectors in which foreign sequences are cloned into phage gene III and displayed as part of the gene III protein (pIII) at one tip of the virion. Each phage encodes a single random sequence and expresses it as a fusion complex with pIII, a minor coat protein present at about five molecules per phage. For example, in the fusion phage techniques of J. K. Scott & G. P. Smith, supra, a library was constructed of phage containing a variable cassette of six amino acid residues. The hexapeptide modules fused to bacteriophage proteins provided a library for the screening methodology that can examine >$10^{12}$ phages (or about $10^8$–$10^{10}$ different clones) at one time, each with a test sequence on the virion surface. The library obtained was used to screen monoclonal antibodies specific for particular hexapeptide sequences. The fusion phage system has also been used by other groups, and libraries containing longer peptide inserts have been constructed. Fusion phage prepared according to this methodology can be selected randomly or non-randomly for inclusion in the array of antigens. The fusion phages selected for inclusion in the array can be propagated by standard methods to result in what is virtually an endless supply of the selected antigens.

Other methods for producing antigens are also known in the art. For example, expression libraries can be prepared by random cloning of DNA fragments or cDNA into an expression vector. E.g., R. A. Young & R. W. Davis, Yeast RNA Polymerase II Genes: Isolation with Antibody Probes, 222 Science 778–782 (1983); G. M. Santangelo et al., Cloning of Open Reading Frames and Promoters from the *Saccharomyces cerevisiae* Genome: Construction of Genomic Libraries of Random Small Fragments, 46 Gene 181–186 (1986). Expression vectors that could be used for making such libraries are commercially available from a variety of sources. For example, random fragments of HeLa cell DNA or cDNA can be cloned into an expression vector, and then clones expressing HeLa cell proteins can be selected. These clones can then be propagated by methods well known in the art. The expressed proteins are then isolated or purified and can be used in the making of the array.

Alternatively, antigens can be synthesized using recombinant DNA technology well known in the art. Genes that code for many viral, bacterial, and mammalian proteins have been cloned, and thus large quantities of highly pure proteins can be synthesized quickly and inexpensively. For example, the genes that code for many eukaryotic and mammalian membrane-bound receptors, growth factors, cell adhesion molecules, and regulatory proteins have been cloned and are useful as antigens. Many proteins produced by such recombinant techniques, such as transforming growth factor a, acidic and basic fibroblast growth factors, interferon, insulin-like growth factor, and various interleukins from different species, are commercially available.

In most instances, the entire polypeptide need not be used as an antigen. For example, any size or portion of the polypeptide that contains at least one epitope, i.e. antigenic determinant or portion of an antigen that specifically interacts with an antibody, will suffice for use in the array.

The antigens, whether selected randomly or non-randomly, are disposed on the solid support to result in the array. The pattern of the antigens on the solid support should be reproducible. That is, the location and identity of each antigen on the solid support should be known. For example, in a 10×10 array one skilled in the art might place antigens 1–100 in locations 1–100, respectively, of the array.

The proteins may placed in arrays on the surface of the solid support using a pipetting device or a machine or device configured for placing liquid samples on a solid support, for example, using a commercially available microarrayer, such as those from Cartesian Technologies, Inc. (Irvine, Calif.); Gene Machines (San Carlos, Calif.); Genetic MicroSystems (Woburn, Mass.); GenePack DNA (Cambridge, UK); Genetix Ltd. (Christchurch, Dorset, UK); and Packard Instrument Company (Meriden, Conn.).

Relevant methods to array a series of protein antigens onto a surface include non-contact drop on demand dispensing and inkjet technology. Commercially available instruments are available for both methods. Cartesian technologies offers several nanoliter dispensing instruments that can dispense liquid volumes from 20 nL up to 250 µL from 96, 384, 1536, 3456, and 9600 well microtiter plates and place them precisely on a surface with densities up to 400 spots/cm$^2$. The instruments will spot onto surfaces in a variety of patterns. As the name implies, inkjet technology utilizes the same principles as those used in inkjet printers. Microfab Technologies offers a 10 fluid print head that can dispense picoliter quantities of liquids onto a surface in a variety of patterns. An illustrative pattern for the present application would be a simple array ranging from 10×10 up to 100×100.

There are a number of methods that can be used to attach proteins or other antigens to the surface of a solid support. The simplest of these is simple adsorption through hydrophobic, ionic, and van der Waals forces. This method is not optimal, however, since the proteins tend to detach from the surface over time. A preferred attachment chemistry involves the use of bifunctional organosilanes. E.g, Thompson and Maragos, 44 J. Agric. Food Chem. 1041–1046 (1996). One end of the organosilane reacts with exposed —OH groups on the surface of the chip to form a silanol bond. The other end of the organosilane contains a group that is reactive with various groups on the protein surface such as —NH$_2$ and —SH groups. This method of attaching proteins to the chip results in the formation of a covalent linkage between the protein and the chip. Other preferred methods that have been used for protein attachment to surfaces include arylazide, nitrobenzyl, and diazirine photochemistry methodologies. Exposure of the above chemicals to UV light causes the formation of reactive groups that can react with proteins to form a covalent bond. The arylazide chemistry forms a reactive nitrene group that can insert into C—H bonds, while the diazirine chemistry results in a reactive carbene group. The nitrobenzyl chemistry is referred to as caging chemistry whereby the caging group inactivates a reactive molecule. Exposure to UV light frees the molecule and makes it available for reaction. Still other methods for attaching proteins to solid supports are well known in the art, e.g., S. S. Wong, Chemistry of Protein Conjugation and Cross-Linking (CRC Press, 340 pp., 1991).

Following attachment of the antigens on the solid support in the selected array, the solid support should be washed by rinsing with an appropriate liquid to remove unbound antigens. Appropriate liquids for washing include phosphate buffered saline (PBS) and the like, i.e. relatively low ionic strength, biocompatible salt solutions buffered at or near neutrality. Many of such appropriate wash liquids are known in the art or can be devised by a person skilled in the art without undue experimentation. E.g., N. E. Good & S. Izawa, Hydrogen Ion Buffers, 24 Methods Enzymology 53–68 (1972).

The solid support is then processed for blocking of nonspecific binding of proteins and other molecules to the solid support. This blocking step prevents the binding of antigens, antibodies, and the like to the solid support wherein such antigens, antibodies, or other molecules are not intended to bind. Blocking reduces the background that might swamp out the signal, thus increasing the signal-to-noise ratio. The solid support is blocked by incubating the solid support in a medium that contain inert molecules that bind to sites where nonspecific binding might otherwise occur. Examples of suitable blockers include bovine serum albumin, human albumin, gelatin, nonfat dry milk, polyvinyl alcohol, Tween 20, and various commercial blockers, such as SEA BLOCK® (trademark of East Coast Biologics, Inc., Berwick, Me.) and SuperBlock™ (trademark of Pierce Chemical Co., Rockford, Ill.) blocking buffers.

Following washing for removal of unbound antigens from the array and blocking, the solid support is contacted with a liquid sample to be tested. The sample can be from any animal that generates individual specific antibodies. For example, humans, dogs, cats, mice, horses, cows, and rabbits have all been shown to possess ISAs. The sample can be from various bodily fluids and solids, including blood, saliva, semen, serum, plasma, urine, amniotic fluid, pleural fluid, cerebrospinal fluid, and mixtures thereof. These samples are obtained according to methods well known in the art. Depending on the detection method used, it may be required to manipulate the biological sample to attain optimal reaction conditions. For example, the ionic strength or hydrogen ion concentration or the concentration of the biological sample can be adjusted for optimal immune complex formation, enzymatic catalysis, and the like.

As described in detail in U.S. Pat. No. 5,270,167 to Francoeur, when ISAs are allowed to react with a set of random antigens, a certain number of immune complexes form. For example, using a panel of about 1000 unique antigens, about 30 immune complexes between ISAs in a biological sample that has been diluted 20-fold can be detected. If the biological sample is undiluted, the total number of possible detectable immune complexes that could form would be greater than $10^{23}$. The total number of possible immune complexes can also be increased by selecting "larger" antigens, i.e. proteins instead of peptides) that have multiple epitopes. Therefore, it will be appreciated that depending on the antigens and number thereof used, the dilution of the biological sample, and the detection method, one skilled in the art can regulate the number of immune complexes that will form and be detected. The set of unique immune complexes that form and fail to form between the ISAs in the biological sample and the antigens in the array constitute an antibody profile.

Methods for detecting antibody/antigen or immune complexes are well known in the art. The present invention can be modified by one skilled in the art to accommodate the various detection methods known in the art. The particular detection method chosen by one skilled in the art depends on several factors, including the amount of biological sample available, the type of biological sample, the stability of the biological sample, the stability of the antigen, and the affinity between the antibody and antigen. Moreover, as discussed above, depending on the detection methods chosen, it may be required to modify the biological sample.

While these techniques are well known in the art, examples of a few of the detection methods that could be used to practice the present invention are briefly described below.

There are many types of immunoassays known in the art. The most common type of immunoassay is competitive and non-competitive heterogeneous assays, such as enzyme-linked immunosorbent assays (ELISA). In a non-competitive ELISA, unlabeled antigen is bound to a solid support, such as the surface of the biochip. Biological sample is combined with antigens bound to the reaction vessel, and antibodies (primary antibodies) in the biological sample are allowed to bind to the antigens, thus forming the immune complexes. After the immune complexes have formed, excess biological sample is removed and the biochip is washed to remove nonspecifically bound antibodies. The immune complexes are then reacted with an appropriate enzyme-labeled anti-immunoglobulin (secondary antibody). The secondary antibody reacts with antibodies in the immune complexes, not with other antigens bound to the biochip. Secondary antibodies specific for binding antibodies of different species, including humans, are well known in the art and are commercially available, such as from Sigma Chemical Co. (St. Louis, Mo.) and Santa Cruz Biotechnology (Santa Cruz, Calif.). After a second wash step, the enzyme substrate is added. The enzyme linked to the secondary antibody catalyzes a reaction that converts the substrate into a product. When excess antigen is present, the amount of product is directly proportional to the amount of primary antibodies present in the biological sample. Preferably, the product is fluorescent or luminescent, which can be measured using technology and equipment well known in the art. It is also possible to use reaction schemes that result in a colored product, which can be measured spectrophotometrically, but such colorimetric reactions are not preferred.

Sandwich or capture assays can also be used to identify and quantify immune complexes. Sandwich assays are a mirror image of non-competitive ELISAs in that antibodies are bound to the solid phase and antigen in the biological sample is measured. These assays are particularly useful in detecting antigens, having multiple epitopes, that are present at low concentrations. This technique requires excess antibody to be attached to a solid phase, such as the biochip. The bound antibody is then incubated with the biological samples, and the antigens in the sample are allowed to form immune complexes with the bound antibody. The immune complex is incubated with an enzyme-linked secondary antibody, which recognizes the same or a different epitope on the antigen as the primary antibody. Hence, enzyme activity is directly proportional to the amount of antigen in the biological sample. D. M. Kemeny & S. J. Challacombe, ELISA and Other Solid Phase Immunoassays (1988).

Typical enzymes that can be linked to secondary antibodies include horseradish peroxidase, glucose oxidase, glucose-6-phosphate dehydrogenase, alkaline phosphatase, β-galactosidase, and urease. Secondary antigen-specific antibodies linked to various enzymes are commercially available from, for example, Sigma Chemical Co. and Amersham Life Sciences (Arlington Heights, Ill.).

Competitive ELISAs are similar to noncompetitive ELISAs except that enzymelinked antibodies compete with unlabeled antibodies in the biological sample for limited antigen binding sites. Briefly, a limited number of antigens are bound to the solid support. Biological sample and enzyme-labeled antibodies are added to the solid support. Antigen-specific antibodies in the biological sample compete with enzyme-labeled antibodies for the limited number of antigens bound to the solid support. After immune complexes have formed, nonspecifically bound antibodies are removed by washing, enzyme substrate is added, and the enzyme activity is measured. No secondary antibody is required. Because the assay is competitive, enzyme activity is inversely proportional to the amount of antibodies in the biological sample.

An alternative competitive ELISA can also be used within the scope of the present invention. In this alternative embodiment, limited amounts of antibodies from the biological sample are bound to the surface of the solid support as described herein. Labeled and unlabeled antigens are then brought into contact with the solids support such that the labeled and unlabeled antigens compete with each other for binding to the antibodies on the surface of the solid support. After immune complexes have formed, nonspecifically bound antigens are removed by washing. The immune complexes are detected by incubation with an enzyme-linked secondary antibody, which recognizes the same or a different epitope on the antigen as the primary antibody, as described above. The activity of the enzyme is then assayed, which yields a signal that is inversely proportional to the amount of antigen present.

Homogeneous immunoassays can also be used when practicing the method of the present invention. Homogeneous immunoassays may be preferred for detection of low molecular weight compounds, such as hormones, therapeutic drugs, and illegal drugs that cannot be analyzed by other methods, or compounds found in high concentration. Homogeneous assays are particularly useful because no separation step is necessary. R. C. Boguslaski et al., Clinical Immunochemistry: Principles of Methods and Applications (1984).

In homogeneous techniques, bound or unbound antigens are enzyme-linked. When antibodies in the biological sample bind to the enzyme-linked antigen, steric hindrances inactivate the enzyme. This results in a measurable loss in enzyme activity. Free antigens (i.e., not enzyme-linked) compete with the enzyme-linked antigen for limited antibody binding sites. Thus, enzyme activity is directly proportional to the concentration of antigen in the biological sample.

Enzymes useful in homogeneous immunoassays include lysozyme, neuraminidase, trypsin, papain, bromelain, glucose-6-phosphate dehydrogenase, and β-galactosidase. T. Persoon, Immunochemical Assays in the Clinical Laboratory, 5 Clinical Laboratory Science 31 (1992). Enzyme-linked antigens are commercially available or can be linked using various chemicals well known in the art, including glutaraldehyde and maleimide derivatives.

Prior antibody profiling technology involves an alkaline phosphatase labeled secondary antibody with 5-bromo-4-chloro-3'-indolylphosphatep-toluidine salt (BCIP) and nitroblue tetrazolium chloride (NBT), both of which are commercially available from a variety of sources, such as from Pierce Chemical Co. (Rockford, Ill.). The enzymatic reaction forms an insoluble colored product that is deposited on the surface of the membrane strips to form bands wherever antigen-antibody complexes occur. This method is suboptimal in a biochip format since it is difficult to quantify and since colorimetric methods are typically less sensitive than assays base on fluorescence or luminescence.

Fluorescent immunoassays can also be used when practicing the method of the present invention. Fluorescent immunoassays are similar to ELISAs except the enzyme is substituted for fluorescent compounds called fluorophores or fluorochromes. These compounds have the ability to absorb energy from incident light and emit the energy as light of a longer wavelength and lower energy. Fluorescein and rhodamine, usually in the form of isothiocyanates that can be readily coupled to antigens and antibodies, are most commonly used in the art. D. P. Stites et al., Basic and Clinical Immunology (1994). Fluorescein absorbs light of 490 to 495 nm in wavelength and emits light at 520 nm in wavelength. Tetramethylrhodamine absorbs light of 550 nm in wavelength and emits light of 580 nm in wavelength. Illustrative fluorescence-based detection methods include ELF-97 alkaline phosphatase substrate (Molecular Probes Inc., Eugene, Oreg.); PBXL1 and PBXL-3 (phycobilisomes conjugated to streptavidin) (Martek Biosciences Corp., Columbia, Md.); FITC and Texas Red labeled goat anti-human IgG (Jackson ImmunoResearch Laboratories, Inc., West Grove, Pa.); and B-Phycoerythrin and R-Phycoerythrin conjugated to streptavidin (Molecular Probes Inc.). ELF-97 is a nonfluorescent chemical that is digested by alkaline phosphatase to form a fluorescent molecule. Because of turn over of the alkaline phosphatase, use of the ELF-97 substrate results in signal amplification. Fluorescent molecules attached to secondary antibodies do not exhibit this amplification.

Phycobiliproteins isolated from algae, porphyrins, and chlorophylls, which all fluoresce at about 600 nm, are also being used in the art. I. Hemmila, Fluoroimmunoassays and Immunofluorometric Assays, 31 Clin. Chem. 359 (1985); U.S. Pat. No. 4,542,104. Phycobiliproteins and derivatives thereof are commercially available under the names R-phycoerythrin (PE) and Quantum Red™ from, for example, Sigma Chemical Co.

In addition, Cy-conjugated secondary antibodies and antigens are useful in immunoassays and are commercially available. Cy-3, for example, is maximally excited at 554 nm and emits light of between 568 and 574 nm. Cy-3 is more hydrophilic than other fluorophores and thus has less of a tendency to bind nonspecifically or aggregate. Cy-conjugated compounds are commercially available from Amersham Life Sciences.

Illustrative luminescence-based detection methods include CSPD and CDP star alkaline phosphatase substrates (Roche Molecular Biochemicals); and SuperSignal® horseradish peroxidase substrate (Pierce Chemical Co., Rockford, Ill.).

Chemiluminescence, electroluminescence, and electrochemiluminescence (ECL) detection methods are also attractive means for quantifying antigens and antibodies in a biological sample. Luminescent compounds have the ability to absorb energy, which is released in the form of visible light upon excitation. In chemiluminescence, the excitation source is a chemical reaction; in electroluminescence the excitation source is an electric field; and in ECL an electric field induces a luminescent chemical reaction.

Molecules used with ECL detection methods generally comprise an organic ligand and a transition metal. The organic ligand forms a chelate with one or more transition metal atoms forming an organometallic complex. Various organometallic and transition metal-organic ligand complexes have been used as ECL labels for detecting and quantifying analytes in biological samples. Due to their thermal, chemical, and photochemical stability, their intense emissions and long emission lifetimes, ruthenium, osmium, rhenium, iridium, and rhodium transition metals are favored in the art. The types of organic ligands are numerous and include anthracene and polypyridyl molecules and heterocyclic organic compounds. For example, bipyridyl, bipyrazyl, terpyridyl, and phenanthrolyl, and derivatives thereof, are common organic ligands in the art. A common organometallic complex used in the art includes tris-bipyridine ruthenium(II), commercially available from IGEN, Inc. (Rockville, Md.) and Sigma Chemical Co.

Advantageously, ECL can be performed under aqueous conditions and under physiological pH, thus minimizing biological sample handling. J. K. Leland et al., Electrogenerated Chemiluminescence: An Oxidative-Reduction Type ECL Reactions Sequence Using Triprophyl Amine, 137 J. Electrochemical Soc. 3127–3131 (1990); WO 90/05296; U.S. Pat. No. 5,541,113. Moreover, the luminescence of these compounds may be enhanced by the addition of various cofactors, such as amines.

In practice, a tris-bipyridine ruthenium(II) complex, for example, may be attached to a secondary antibody using strategies well known in the art, including attachment to lysine amino groups, cysteine sulfhydryl groups, and histidine imidazole groups. In a typical ELISA immunoassay, secondary antibodies would recognize ISAs bound to antigens, but not unbound antigens. After washing nonspecific binding complexes, the tris-bipyridine ruthenium(II) complex would be excited by chemical, photochemical, and electrochemical excitation means, such as by applying current to the biochip. E.g., WO 86/02734. The excitation would result in a double oxidation reaction of the tris-bipyridine ruthenium(II) complex, resulting in luminescence that could be detected by, for example, a photomultiplier tube. Instruments for detecting luminescence are well known in the art and are commercially available, for example, from IGEN, Inc.

Solid state color detection circuitry can also be used to monitor the color reactions on the biochip and, on command, compare the color patterns before and after the sample application. A color camera image can also be used and the pixel information analyzed to obtain the same information.

Still another method involves detection using a surface plasmon resonance (SPR) chip. The surface of the chip is scanned before and after sample application and a comparison is made. The SPR chip relies on the refraction of light when the molecules of interest are exposed to a light source. Each molecule has its own refraction index by which it can be identified. This method requires precise positioning and control circuitry to scan the chip accurately.

Yet another method involves a fluid rinse of the biochip with a fluorescing reagent. The microlocations that combine with the biological sample will fluoresce and can be detected with a charge-coupled device (CCD) array. The output of such a CCD array is analyzed to determine the unique pattern associated with each sample. This approach avoids the problems associated with scanning technologies. Speed is not a factor with any of the methods since the chemical combining of sample and reference takes minutes to occur.

Moreover, array scanners are commercially available, such as from Genetic MicroSystems. The GMS 418 Array Scanner uses laser optics to rapidly move a focused beam of light over the biochip. This system uses a dual-wavelength system including high-powered, solid-state lasers that generate high excitation energy to allow for reduced excitation time. At a scanning speed of 30 Hz, the GMS 418 can scan a 22×75-mm slide with 10-$\mu$m resolution in about 4 minutes.

Software for image analysis obtained with an array scanner is readily available. Available software packages include ImaGene (BioDiscovery, Los Angeles, Calif.); ScanAlyze (available at no charge; developed by Mike Eisen, Stanford University); DeArray (developed by Yidong Chen and Jeff Trent of the National Institutes of Health; used with IP Lab from Scanalytics, Fairfax, Va.); Pathways (Research Genetics, Huntsville, Ala.); GEM tools (Incyte Pharmaceuticals, Inc., Palo Alto, Calif.); and Imaging Research (Amersham Pharmacia Biotech, Inc., Piscataway, N.J.).

Once interactions between the antigens and ISAs have been identified and quantified, the signals may be digitized. The digitized antibody profile serves as a signature that identifies the source of the biological sample. Depending on the biochip used, the digitized data may take numerous forms. For example, the biochip may comprise an array with 10 columns and 10 rows for a total number of 100 microlocations. Each microlocation contains at least one antigen. After the biological sample containing the ISAs is added to each microlocation and allowed to incubate, interactions between antigens and ISAs in the biological sample are identified and quantified. In each microlocation, an interaction between the antigen at that microlocation and the ISAs in the biological sample either do or do not result in a quantifiable signal. In one preferred embodiment, the results of the antibody profile are digitized by ascribing each one of the 100 microlocations a numerical value of either "0," if a quantifiable signal was not obtained, or "1," if a quantifiable signal was obtained. Using this method, the digitized antibody profile comprises a unique set of 0's and 1's.

The numerical values "0" or "1" will, of course, preferably be normalized to signals obtained in internal control microlocations so that digitized antibody profiles obtained at a later time can be properly compared. For example, one or several of the microlocations will contain a known antigen, which will remain constant over time. Therefore, if subsequent biological sample is more or less dilute than a previous biological sample, the signals can be normalized using the signals from the known antigen.

It will be appreciated by one skilled in the art that other methods of digitizing the antibody profile exist and may be used. For example, rather than ascribing each microlocation with a numerical value of "0" or "1," the numerical value may be incremental and directly proportional to the strength of the signal.

By digitizing the antibody profile signals, the biochemical results can be entered into a computer and quickly accessed and referenced. Within seconds of having the antibody profile digitized, a computer can compare a previously digitized antibody profile to determine whether there is a match. If a matching antibody profile is in the database, a positive identification of the source of the biological sample can be made. Thus, the method of the present invention can both discriminate and positively identify the source of a biological sample.

In a preferred embodiment of the invention, the present method is used for forensic analysis for matching a biological sample to a criminal suspect. Forensic samples obtained from crime scenes are often subject to drying of the samples, small sample sizes, mixing with samples from more than one individual, adulteration with chemicals, and the like. The present method provides the advantages of rapid analysis, simplicity, low cost, and accuracy for matching forensic samples with suspects. For example, the forensic sample and a sample from one or more suspects are obtained according to methods well known in the art. Antibody profiles for each of the samples are prepared, as described herein. The antibody profiles are then compared. A match of antibody profiles means that the forensic sample was obtained from the matching suspect. If no match of antibody profiles is obtained, then none of the suspects was the source of the forensic sample.

In another preferred embodiment of the invention, the present method is used for drug testing of individuals. For example, in many work places it is a condition of obtaining or maintaining employment to be free of illegal drug use. The presence of illegal drugs in the bloodstream of a person can be detected by the present method by antibody capture or similar methods. Moreover, as described in WO 97/29206, the drug test and the identity of the sample can be correlated in a single test. Drug tests are also important in certain animals, such as horses and dogs involved in racing.

EXAMPLE 1

The law enforcement community has demonstrated several needs associated with drug testing of suspects including dealing with privacy issues associated with sample collection, maintenance of sample chain of custody, prevention of sample adulteration by the suspect, and facilitating more rapid turn around time on sample analyses. Current drug testing protocols utilize urine samples and, occasionally, blood samples. Invasion of privacy is a continuing problem with urine samples since it is necessary to observe the individual providing the sample to maintain the chain of custody and eliminate the possibility of sample switching or adulteration. Urine samples are also not a good indicator of the current level of intoxication since many drug metabolites continue to be excreted into urine for days or weeks after the drugs are initially taken. While blood samples do not suffer from these problems, collecting blood is an invasive procedure requiring special facilities and trained personnel that may not always be available when the need arises. It is necessary for law enforcement personnel to maintain strict chain of custody for all samples collected to ensure that mishandling or deliberate tampering do not occur. A break or even a perceived break in the chain of custody can result in evidence being dismissed outright or given little weight.

The present invention solves these issues in several ways. First, incorporation of the antibody profiling identification assay into the drug test makes identification of the sample donor integral to the test and eliminates the need for complex chain of custody procedures. Second, a saliva-based drug test is better than a urine test because drug levels in saliva can be readily correlated with drug levels in blood (W. Schramm et al., Drugs of Abuse in Saliva: A Review, 16 J. Anal. Toxicology 1–9 (1992); E. J. Cone, Saliva Testing for Drugs of Abuse, 694 Ann. N.Y. Acad. Sci. 91–127 (1995)), therefore providing a better indicator of current drug use (D. A. Kidwell et al., Testing for drugs of abuse in saliva and sweat, 713 J. Chrom. B 111–135 (1998)). Saliva samples from a suspect can also be collected easily in view of a law enforcement officer without invasion of privacy or with invasive methods. Finally, the present test is easy to use and can be quickly performed by law enforcement personnel on site, instead of requiring the days to weeks necessary at distant centralized laboratories. V. S. Thompson et al., Antibody profiling as an identification tool for forensic samples, 3576 Investigation and Forensic Science Technologies 52–59 (1999).

In this example, an antibody-based test is provided for two common illicit drugs (cocaine and methamphetamine). These drugs are among the most commonly abused, and their use is on the rise. S. B. Karch, Drug Abuse Handbook (CRC Press, 1998); L. D. Bowers, Athletic Drug Testing, 17 Sports Pharmacology 299–318 (1998).

Materials and Methods Goat anti-rabbit IgG antibodies conjugated to alkaline phosphatase were obtained from Jackson Immunoresearch (West Grove, Pa.). Rabbit anti-human IgA antibodies were purchased from U.S. Biological (Swampscott, Mass.). Seablock™, nitro-blue tetrazolium chloride/5-bromo-4-chloro-3'-indolylphosphate p-toluidine salt (NBT/BCIP), p-nitrophenyl phosphate disodium salt (PNPP), EZ-Link™ maleimide activated alkaline phosphatase kits, and FreeZyme® conjugate purification kits were obtained from Pierce Chemical (Rockford, Ill.). Monoclonal antibodies against benzoylecgonine and methamphetamine, and bovine serum albumin (BSA) conjugates of methamphetamine and benzoylecgonine were purchased from O.E.M Concepts (Toms River, N.J.). Cocaine and methamphetamine hydrochloride salts were obtained from Sigma-Aldrich (St. Louis, Mo.). Antibody Profiling strips were purchased from Miragen, Inc. (Irvine, Calif.). Strips used for the combined drug-AbP test were produced according to the protocol of A. M. Francoeur, Antibody fingerprinting: a novel method for identifying individual people and animals, 6 Bio/Technology 822–825 (1988). Saliva samplers from Saliva Diagnostic Systems (Vancouver, Wash.), Ora Sure Technologies, Inc. (Bethlehem, Pa.), and Sarstedt, Inc. (Newton, N.C.) were used to collect saliva samples from volunteers.

A saliva-based AbP assay was developed through modification of an earlier protocol designed for processing blood samples. T. F. Unger & A. Strauss, Individual-specific antibody profiles as a mean of newborn infant identification, 15 J. Perinatology 152–155 (1995). Briefly, 500 µl of saliva sample diluted with 1.0 ml of PBST (50 mM phosphate buffered saline, 0.2% Tween 20) was incubated with an AbP strip overnight for a minimum of 16 hours, and excess sample was washed off with PBST. Next, the strip was incubated successively with 100 ng/ml rabbit anti-human IgA for 1 hour and 100 ng/ml goat anti-rabbit IgG-alkaline phosphatase conjugate for 30 minutes with wash steps in between incubations. The strip was washed again with PBST and a precipitation substrate for alkaline phosphatase, NBT/BCIP, was added to allow development of bands on the strip.

The Saliva Sampler™ (Saliva Diagnostic Systems) and the Saliveffe™ (Sarstedt, Inc.) saliva collection systems were examined for compatibility with the AbP assay. The Saliva Sampler™ system comprises a cotton pad attached to a plastic handle. A window in the handle turns blue when sufficient sample has been collected. The pad is placed in a preservative buffer after collection. The Salivette™ is a cotton roll placed in the mouth for about 10 minutes and then centrifuged in a plastic tube to collect sample. Both types of samplers were placed in the gingival crevice of the mouth for sample collection. The quality of samples as a function of storage time at temperatures of −20° C., 4° C., and 25° C. was assessed by performing AbP on samples collected with both samplers.

Five volunteers participated in studies to compare blood AbP patterns with those obtained from saliva samples. Protocols for use of human subjects were conducted in accordance with the Idaho National Engineering and Environmental Laboratory Institutional Review Board. Blood samples were collected in tubes containing the anticoagulant EDTA and were used immediately. Saliva was collected using the Saliva Sampler™ saliva collection system. Paired blood and saliva samples were analyzed using the blood protocol of Unger & Strauss, supra, and the saliva AbP test described above.

Four additional volunteers participated in a saliva adulteration study to assess the effects of various foods and beverages on the AbP assay. The volunteers were given butterscotch and lemon hard candy, sugar and sugar-free gum, sugar and sugar-free cola, and milk chocolate. After eating the above, they were asked to collect saliva samples using the provided saliva samplers. Volunteers were also asked to consume alcohol, drink coffee, eat a food of their choice, and brush their teeth prior to giving samples. A volunteer who was a smoker provided a sample after smoking a cigarette. Baseline samples were also collected from the volunteers.

Monoclonal antibodies against methamphetamine and benzoylecgonine were conjugated to alkaline phosphatase using the Pierce EZ-Link™ maleimide activated alkaline phosphatase kit according to the manufacturer's protocols. Unconjugated antibody was separated from the antibody-enzyme conjugate using the FreeZyme® conjugate purification kit according to the manufacturer's protocols.

Competitive enzyme linked immunosorbent assays (ELISAs) were developed for both cocaine and methamphetamine. The BSA conjugates of methamphetamine or benzoylecgonine were diluted in 50 mM carbonate buffer, pH 9.6, and 50 µl was added to each well of a 96-well microtiter plate. The plate was incubated overnight at 4° C. to allow the conjugates to bind to the well surfaces. The plate was then washed with PBST to remove excess BSA conjugate. Next, 50 µl of either cocaine or methamphetamine solution in the concentration range from 0 to 1000 µg/ml was added to the plate and 50 µl of either monoclonal anti-benzoylecgonine or anti-methamphetamine conjugated with alkaline phosphatase was added. During this step, the immobilized BSA drug conjugate competed with the free drug in solution for binding sites on the antibodies. After the competition reaction was complete, the unbound antibodies and free drug were washed away. Finally, 100 µl of soluble alkaline phosphatase substrate (PNPP) solution was added to the wells to react with the alkaline phosphatase bound to the well surfaces through the anti-drug antibodies. The reaction was stopped after 20–30 minutes by addition of 25 µl of 3 M NaOH, and the absorbance of each well was read at 405 nm using a Tecan Spectra microplate reader.

Polyvinylidene fluoride (PVDF) membrane is used in the manufacture of the Miragen AbP strips, and was used to assess the feasibility of binding the cocaine-and methamphetamine-BSA conjugates to the its surface. The PVDF membrane was cut into strips the same size as those used in the AbP assay. Four strips were prepared for each drug and 10 µl spots of either drug-BSA conjugate were placed at three locations on each strip for analysis in triplicate. The strips were dried at 35° C. for one hour prior to use. Non-specific binding sites on the strips were blocked with PBST containing 1 mg/mL BSA for one hour and then rinsed with PBST. Cocaine and methamphetamine solutions were prepared in PBST at concentrations of 0, 0.1, 10, and 1000 µg/ml. Next, 750 µl of cocaine or methamphetamine solution were added to the strips and another 750 µl of antibenzoylecgonine or anti-methamphetamine antibodies conjugated with alkaline phosphatase were added and allowed to incubate for one hour. During this time a competitive reaction between the free and immobilized drug for antibody binding sites took place. The strips were washed to remove unbound antibodies and drugs and the NBT/BCIP substrate was added. The strips were allowed to develop for 15 minutes.

A combined AbP-drug assay was prepared by placing 10 µl spots of both methamphetamine and benzoylecgonine-BSA conjugate onto the blank bottom portion of the AbP strip and allowing them to dry for one hour at 35° C. Saliva samples from three individuals were collected using Ora Sure samplers. Half of the saliva sample was spiked with 1000 µg/ml of cocaine or methamphetamine. The strips were blocked with PBST containing 1.0 mg/ml BSA for one hour and rinsed with PBST. Next, 500 µl of spiked or unspiked saliva was added to the strips along with alkaline phosphatase conjugated antibenzoylecgonine and anti-methamphetamine antibodies and allowed to incubate over night at room temperature. The strips were washed with PBST and the AbP assay was conducted as described above.

Results and Discussion. The saliva-based AbP assay was optimized through variation of reagent concentrations, sample volumes, and incubation times. Illustrative results of antibody profiles obtained from saliva samples are shown in FIG. 1. Compared to the blood-based AbP assay, the saliva assay takes much longer (18 hours versus 2 hours) and requires a 10-fold larger amount of sample. This is due to the 100-fold lower levels of total antibody present in saliva as compared to blood. Parry, Tests for HIV and hepatitis viruses, 694 Annals N.Y. Acad. Sci. 221 (1993).

The stability of antibodies present in the saliva samples collected using the Saliva Sampler™ or the Salivette™ systems was determined by storage at −20° C., 4° C., and 25° C. and AbP testing of samples daily over the period of one week to see if there were any changes in the patterns observed. Fresh saliva samples from either sampler gave the best results. The stability over time of samples collected with the Saliva Sampler™ system was superior to samples collected with the Salivette™ system at all temperatures. The preservative storage buffer provided with the Saliva Sampler™ system appears to prevent antibody degradation due to bacterial contamination, while the Salivette™ sampler includes no preservative.

The samples collected with the Saliva Sampler™ system and maintained at room temperature showed no change in pattern over a five-day period. This result is in contrast to the results obtained with samples stored in a refrigerator, which showed marked deterioration even after a few hours of storage. It is not clear why this occurred. Frozen samples also showed some deterioration due to damage caused by freeze-thaw cycles, but prolonged storage at freezing temperatures resulted in no further degradation. Since Saliva Sampler™ saliva collection systems had superior storage properties and were easier to use, they were used for the adulteration studies.

Figure 2:
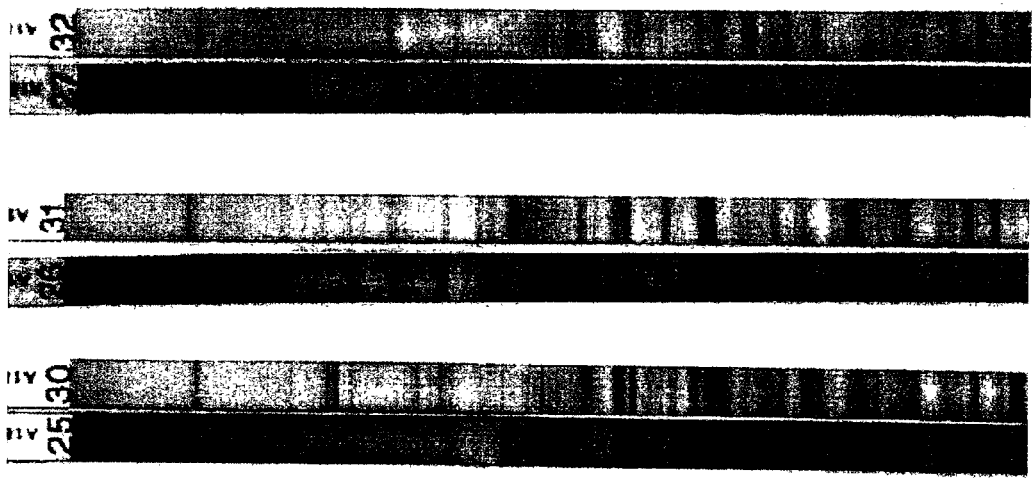
FIG. 2 shows comparisons of paired saliva and blood antibody profiles from five individuals according to the procedure of Example 1.

Blood AbP patterns were compared to saliva AbP patterns to determine if the ISAs present in those samples were the same. The results showed that the patterns obtained from the two different samples differed markedly (FIG. 2). This result was somewhat surprising since saliva is a filtrate of blood, and it was expected that the ISAs present in saliva would be the same as those present in blood. The different patterns probably resulted from the isotype of antibody examined in each case. In blood IgG antibodies were analyzed since they are the most prevalent. In saliva, IgA antibodies are more prevalent and were analyzed. After the above result was obtained, saliva samples were also analyzed for IgG antibodies to determine if those patterns would be the same as those from the blood patterns. However, this was unsuccessful due to the extremely low levels of IgG antibodies present in saliva.

Figure 3:
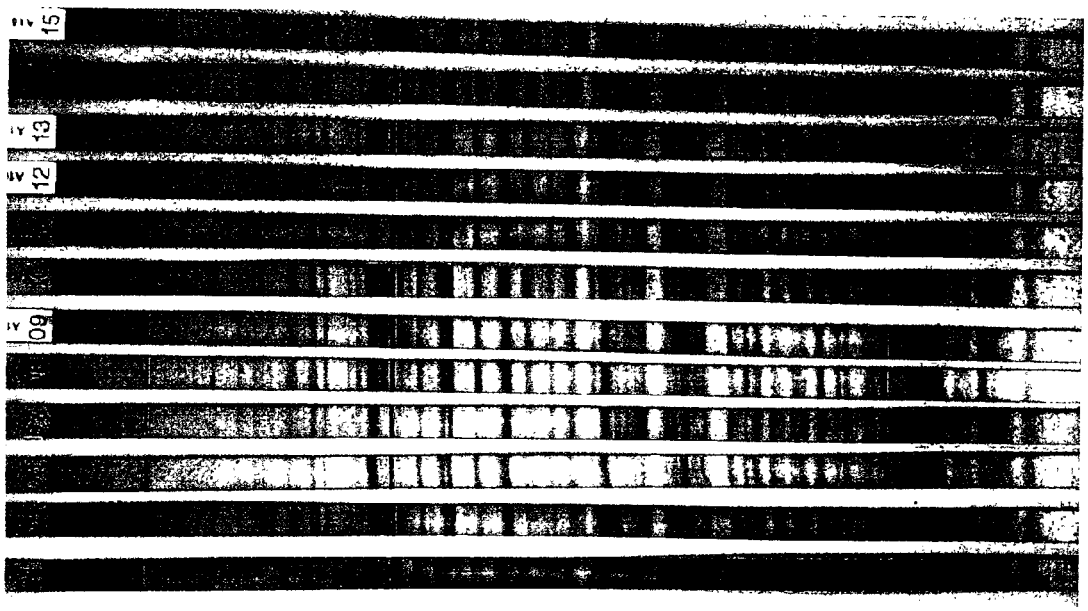
FIG. 3 shows antibody profiles obtained from saliva samples from a single individual after contamination with various adulterants according to the procedure of Example 1.

The saliva adulteration studies showed that virtually no changes occurred in the antibody profiles when any of the adulterants were present (FIG. 3). In some cases a band might be darker or lighter, but there appeared to be no missing or additional bands present. Since this was a preliminary study, the adulterants examined were easily obtainable items that might be used during the course of ordinary life. However, as a quick search of the Internet reveals, there are many proposed methods to beat urine-based drug tests including ingestion of and adulteration of samples with various substances that are being sold by these sites. The adulteration results shown here are promising since it appears that the AbP test is not affected by foods that may be commonly consumed before taking a saliva test.

Figure 4:
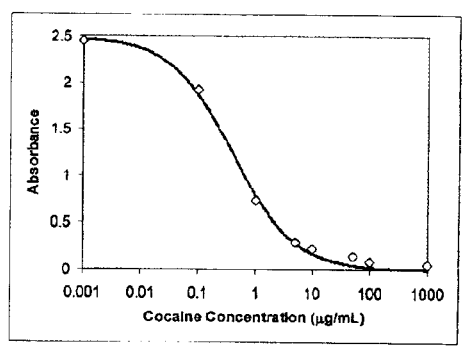
FIG. 4 shows illustrative results obtained from immunoassay of cocaine in saliva samples according to the procedure of Example 1.
Figure 5:
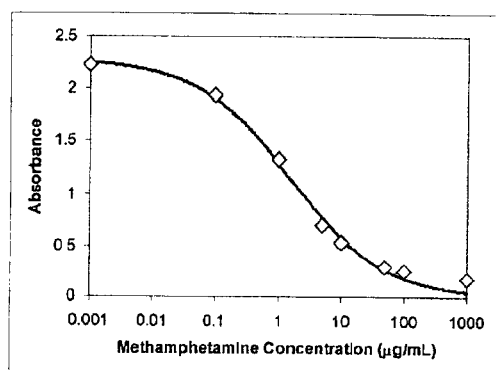
FIG. 5 shows illustrative results obtained from immunoassay of methamphetamine in saliva samples according to the procedure of Example 1.

Immunoassay tests for both cocaine and methamphetamine were developed using a direct competitive assay. An anti-benzoylecgonine antibody was used for the cocaine assay; however, this antibody gave the same response to cocaine as to benzoylecgonine (the primary metabolite of cocaine) so it did not effect the results of the assay. In this assay, drug present in a sample competes for binding sites on enzyme labeled antibodies with a BSA-conjugated drug immobilized to the surface of a well of a microtiter plate. In samples with large drug concentrations, most of the antibody-enzyme conjugate will bind to the drug in solution and will be washed away during the final step. Therefore, there will be very little enzyme present in the microtiter plate and the amount of color development will be low. Conversely, if there is no drug in the sample, the antibodies will bind to the immobilized drugs and stay in the wells after the wash step resulting in strong color development. This results in a signal that is inversely proportional to the drug concentration (FIGS. 4 and 5). The linear range for cocaine detection was from 0.1 to 5 µg/ml and for methamphetamine was from 0.1 to 10 µg/ml. This range covers the cutoff values for these drugs (0.3 and 1.0 µg/ml, respectively) currently set by the Substance Abuse and Mental Health Services Administration. M. Peat & A. E. Davis, Drug Abuse Handbook (CRC Press, Boca Raton, Fla. 1998).

Figure 6:
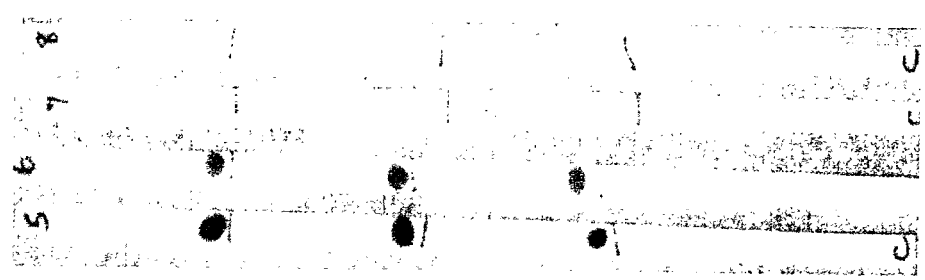
FIG. 6 shows illustrative results of immunodetection of cocaine on a PVDF membrane: strip 5, 0 $\mu$g/ml cocaine; strip 6, 0.1 $\mu$g/ml cocaine; strip 7, 10 $\mu$g/ml cocaine; strip 8, 1000 $\mu$g/ml cocaine.
Figure 7:
FIG. 7 shows illustrative results of immunodetection of methamphetamine on a PVDF membrane: strip 1, 0 $\mu$g/ml methamphetamine; strip 2, 0.1 $\mu$g/ml methamphetamine; strip 3, 10 $\mu$g/ml methamphetamine; strip 4, 1000 $\mu$g/ml methamphetamine.

Using the optimum concentrations of BSA-drug conjugates determined during the ELISA studies, the drug assays were conducted on the PVDF membranes. Because of the inverse relationship of the immunoassay to drug concentration, a dark spot was observed when the concentration of drugs was low, and spots gradually disappeared as the drug concentration increased (FIGS. 6 and 7).

Figure 8:
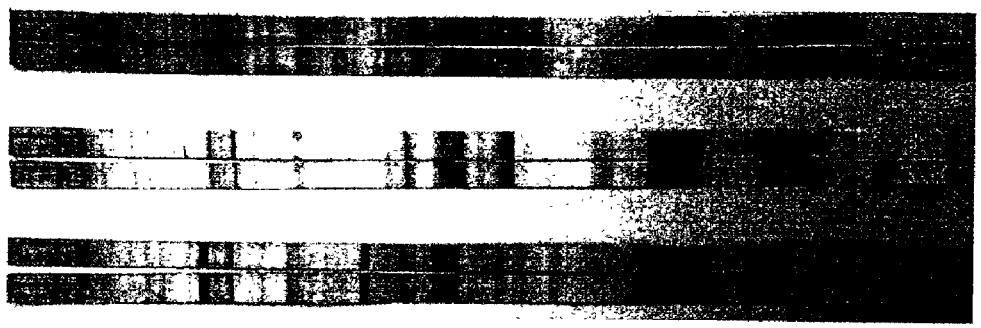
FIG. 8 shows antibody profiles from three different individuals; one strip of each pair contains no drugs, and the other strip of each pair contains 1000 $\mu$g/ml of cocaine and of methamphetamine.

Since the drug test on the PVDF membranes were promising, the feasibility of combining the two drug tests with the AbP assay was assessed. Antibody profile patterns from the three individuals did not change regardless of whether the drug was present or not (FIG. 8). This results shows that the presence of the drugs did not interfere with the reagents used to perform the antibody profiling assay.

EXAMPLE 2

In this example the procedure of Example 1 is followed except that fractionated HeLa cell antigens are immobilized on a PVDF membrane in a predetermined pattern as a two-dimensional array. Additionally, cocaine and methamphetamine are immobilized on the membrane as additional spots on the array. After development of color as described, results are substantially similar to those of Example 1.

EXAMPLE 3

In this example the procedure of Example 2 is followed except that the array is immobilized on a glass slide.

We claim:

1. A method for detecting a selected drug in a biological sample comprising individual specific antibodies and identifying a source of the biological sample, the method comprising:

immobilizing multiple antigens in a pre-selected pattern on a solid support;

immobilizing a detectable amount of a selected drug on the solid support, to form an array;

providing an antibody-enzyme conjugate comprising an antibody configured to bind the selected drug and an enzyme that is capable of converting a colorigenic substrate into a colored product;

contacting the array with a biological sample, to bind at least some of the multiple antigens with individual specific antibodies in the biological sample, to form immune complexes;

contacting the array with the antibody-enzyme conjugate, wherein the antibody-enzyme conjugate competitively binds to (i) the selected drug immobilized on the array, to form an immobilized antibody-enzyme conjugate, and (ii) any selected drug that may be present in the biological sample, to form a soluble drug-antibody-enzyme conjugate;

washing the solid support, to remove at least the soluble drug-antibody-enzyme complexes;

contacting the solid support with a colorigenic substrate to convert the colorigenic substrate to a colored product using the immobilized antibody-enzyme conjugate;

determining an amount of the colored product present, wherein the amount of the colored product may be inversely correlated with an amount of the selected drug in the biological sample; and detecting the immune complexes immobilized on the solid support to form an antibody profile characteristic of the source of the biological sample.

2. The method of claim 1, further comprising comparing the antibody profile to one or more candidate antibody profiles from candidate sources, wherein a match of the antibody profile to the one or more candidate antibody profiles identifies the source of the biological sample.

3. The method of claim 1, wherein immobilizing a detectable amount of the selected drug on the solid support comprises selecting the selected drug from the group consisting of marijuana, cocaine, methamphetamine, amphetamine, heroin, methyltestosterone, mesterolone and combinations thereof.

4. The method of claim 1, wherein contacting the array with a biological sample comprises obtaining a biological sample from a source selected from the group consisting of tissue, blood, saliva, urine, perspiration, tears, semen, serum, plasma, amniotic fluid, pleural fluid, cerebrospinal fluid, and combinations thereof.

5. The method of claim 1, comprising obtaining the biological sample from saliva.

6. The method of claim 1, comprising immobilizing multiple antigens from a HeLa cell.

7. The method of claim 1, comprising immobilizing multiple antigens from a random peptide library.

8. The method of claim 1, comprising immobilizing multiple antigens from an epitope library.

9. The method of claim 1, comprising immobilizing multiple antigens from a random cDNA expression library.

10. The method of claim 1, comprising immobilizing multiple antigens on the solid support, wherein the solid support comprises at least one substance selected from the group of substances consisting of glass, silicon, silica, polymeric material, poly(tetrafluoroethylene), poly(vinylidenedifluoride), polystyrene, polycarbonate, polymethacrylatem, ceramic material, and hydrophilic inorganic material.

11. The method of claim 1, comprising immobilizing multiple antigens on the solid support, wherein the solid support comprises a hydrophilic inorganic material selected from the group consisting of at least one of alumina, zirconia, titania, nickel oxide.

12. The method of claim 1, wherein providing the antibody-enzyme conjugate comprises the antibody conjugated to alkaline phosphatase.

13. The method of claim 1, wherein providing the antibody-enzyme conjugate comprises providing the antibody conjugated to horseradish peroxidase.

14. The method of claim 1, wherein detecting the immune complexes immobilized on the solid support comprises:

contacting the immune complexes with primary antibodies capable of binding the immune complex, wherein the primary antibodies are from a different species than the individual specific antibodies;

removing primary antibodies not bound to the immune complexes;

contacting the primary antibodies bound to the immune complexes with enzyme-conjugated secondary antibodies capable of binding the primary antibodies, wherein the enzyme-conjugated secondary antibodies are from a different species than the individual specific antibodies and the primary antibodies;

removing unbound enzyme-conjugated secondary antibodies; and detecting bound enzyme-conjugated secondary antibodies, to detect the immune complexes on the solid support.

* * * * *